(12) United States Patent
Young et al.

(10) Patent No.: US 10,327,827 B2
(45) Date of Patent: Jun. 25, 2019

(54) TORSIONAL ORTHOPAEDIC REVISION SYSTEM

(71) Applicant: RADLEY SCIENTIFIC LIMITED, South Devon (GB)

(72) Inventors: Michael John Radley Young, South Devon (GB); Stephen Michael Radley Young, South Devon (GB); Michael James Ede, South Devon (GB)

(73) Assignee: RADLEY SCIENTIFIC LIMITED, South Devon (GB)

( * ) Notice: Subject to any disclaimer, the term of this patent is extended or adjusted under 35 U.S.C. 154(b) by 237 days.

(21) Appl. No.: 15/320,604

(22) PCT Filed: Jun. 27, 2015

(86) PCT No.: PCT/GB2015/000201
§ 371 (c)(1),
(2) Date: Dec. 20, 2016

(87) PCT Pub. No.: WO2015/198005
PCT Pub. Date: Dec. 30, 2015

(65) Prior Publication Data
US 2017/0143398 A1  May 25, 2017

(30) Foreign Application Priority Data
Jun. 26, 2014 (GB) .................................. 1411381.5

(51) Int. Cl.
*A61B 17/88* (2006.01)
*A61B 17/32* (2006.01)
(Continued)

(52) U.S. Cl.
CPC ........ *A61B 17/8847* (2013.01); *A61B 17/164* (2013.01); *A61B 17/1659* (2013.01);
(Continued)

(58) Field of Classification Search
CPC ..... A61B 17/88; A61B 17/8847; A61B 17/16; A61B 17/164; A61B 17/1659; A61B 17/32
See application file for complete search history.

(56) References Cited

U.S. PATENT DOCUMENTS

| 4,750,488 A | 6/1988 | Wuchinich et al. |
| 5,697,545 A | 12/1997 | Jennings et al. |

(Continued)

FOREIGN PATENT DOCUMENTS

| WO | 1993003676 | 3/1993 |
| WO | 1996020657 | 7/1996 |

OTHER PUBLICATIONS

International Search Report and Written Opinion issued in PCT/GB2015/000201, dated Oct. 21, 2015.

*Primary Examiner* — Christopher J Beccia
(74) *Attorney, Agent, or Firm* — Heslin, Rothenberg, Farley & Mesiti P.C.

(57) ABSTRACT

A torsional-mode ultrasonic vibration generator is manufactured with longitudinal slots extending along its horn which damp unwanted vibrational modes and allow it to be made significantly smaller than previous apparatus. The torsional-mode ultrasonic generator is operable with a suite of surgical tools, to perform portions of an orthopaedic arthroplasty revision procedure. Three of the tools are for removing bone cement from within a bone cavity on a prosthesis cemented into the bone cavity. Three other tools are for separating an uncemented prosthesis from ingrown bone by cutting the bone between the prosthesis and walls of the bone cavity. The seventh tool is provided with sensors to determine a separation between a bone-cutting tool head and a metal prosthesis, feedback from the sensors being used to control (Continued)

servo motors of an articulated mounting for the seventh tool, to maintain the separation at a desirable value.

20 Claims, 8 Drawing Sheets

(51) Int. Cl.
*A61B 17/16* (2006.01)
*A61F 2/46* (2006.01)
(52) U.S. Cl.
CPC ............... *A61B 17/320068* (2013.01); *A61B 2017/1602* (2013.01); *A61F 2002/4683* (2013.01)

(56) References Cited

U.S. PATENT DOCUMENTS

| | | | |
|---|---|---|---|
| 6,425,906 | B1 | 7/2002 | Young et al. |
| 2010/0100139 | A1 | 4/2010 | Young |

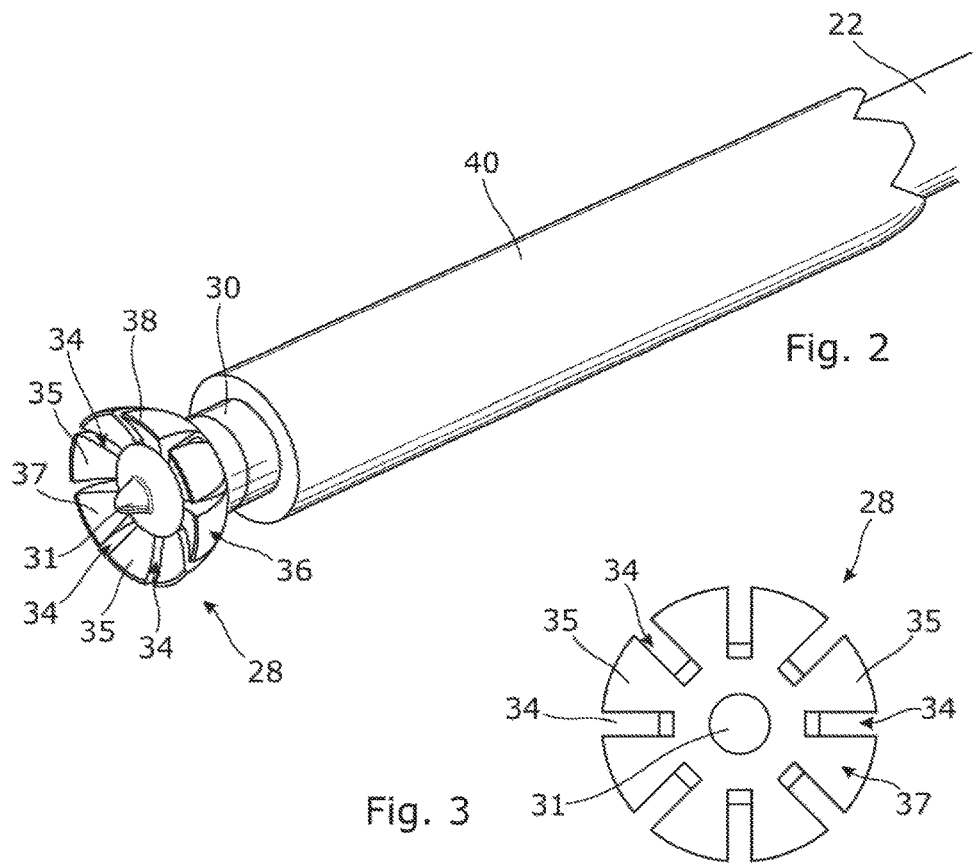
Fig. 2
Fig. 3
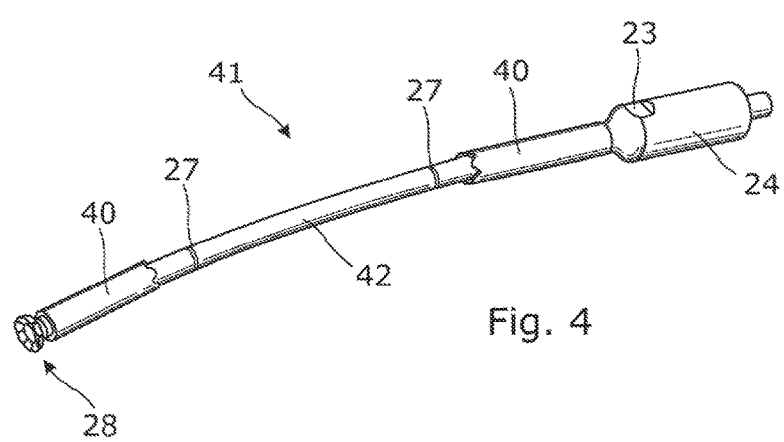
Fig. 4

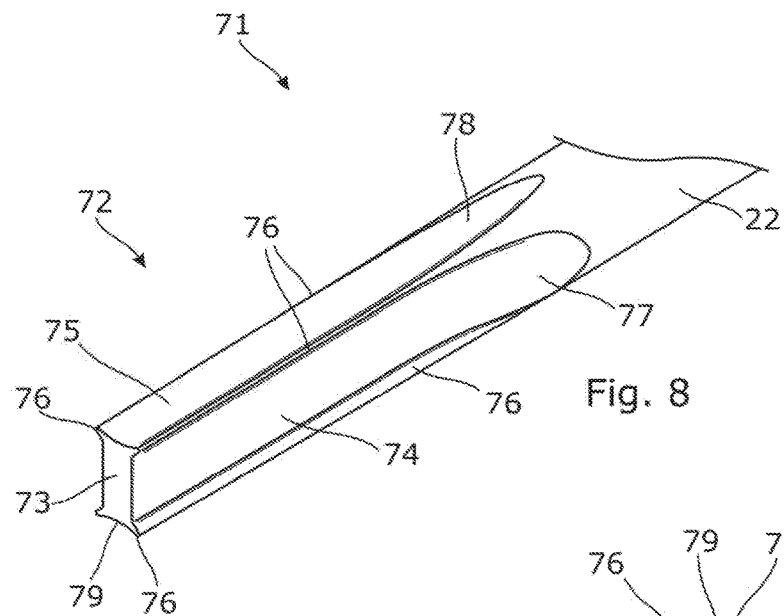
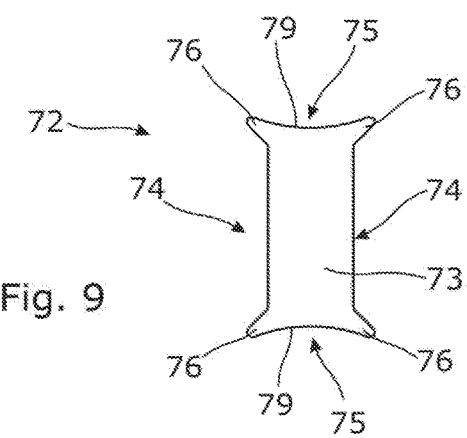
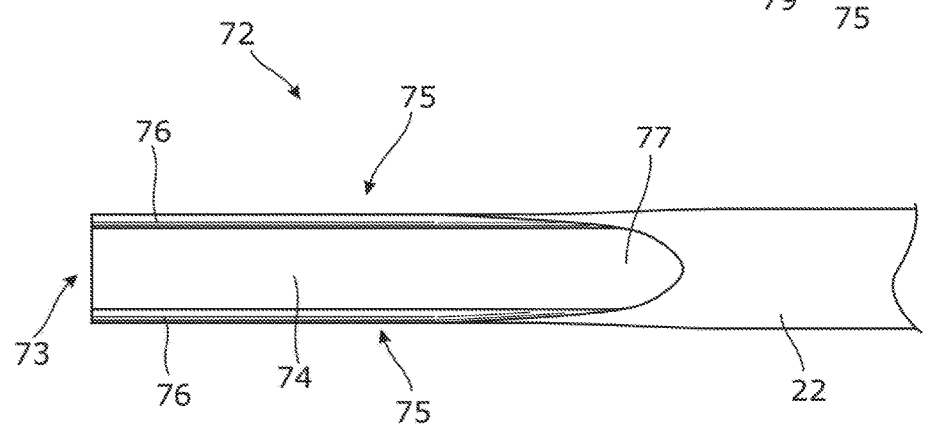

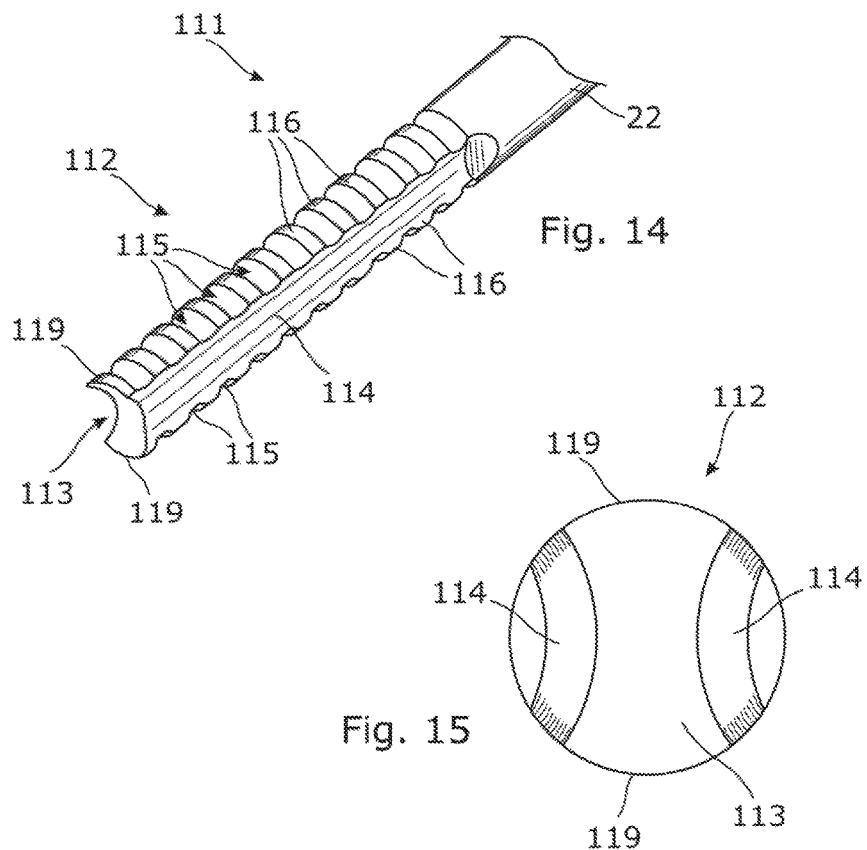
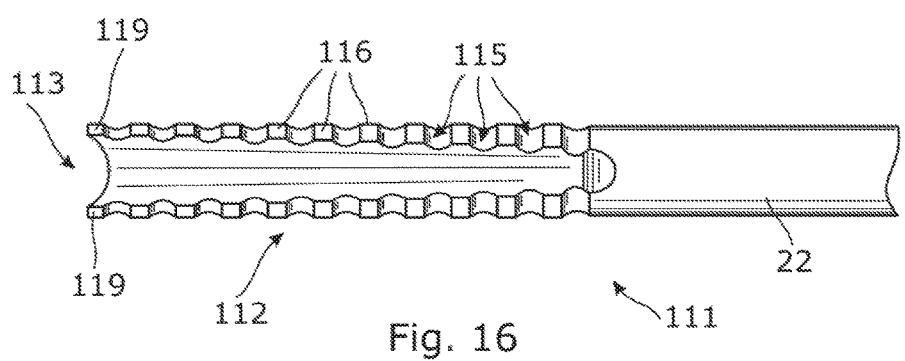

TORSIONAL ORTHOPAEDIC REVISION SYSTEM

CROSS REFERENCE TO RELATED APPLICATIONS

This application is the National Phase filing under 35 U.S.C. § 371 of International Application No. PCT/GB2015/000201, filed on Jun. 27, 2015, and published on Dec. 30, 2015 as WO/2015/198005 A1, and claims priority to Great Britain Application No. 1411381.5, filed on Jun. 26, 2014. The contents of each of the prior applications are hereby incorporated by reference herein in their entirety.

FIELD OF THE INVENTION

The present invention relates to an improved system of surgical equipment for use in orthopaedic surgery. More particularly but not exclusively, it relates to ultrasonically-activatable tools and ultrasound generators for use in the revision of prosthesis implantation and trauma fixation.

BACKGROUND ART

Orthopaedic implants, such as femoral implants for hip joint replacements, are implanted using two main approaches. In one, a cavity within the femur is shaped to receive the shaft of the implant, and following implantation one relies on natural bone regrowth to fill any voids remaining between the implant and the bone. In the other, poly (methylmethacrylate) (PMMA) bone cement is used to coat an internal wall of a similar cavity, and fills any gaps between the implant and the bone when the implant is inserted.

In the first approach, the ingrown bone bonds strongly to the metal of the implant (usually titanium or a specialist steel). In the second, it has been found that the PMMA cement bonds strongly to the bone, but not to the metal implant. However, this is not a drawback, as the healed bone surrounding the implant holds it in place under compression, and at worst the implant may shift in position millimetrically, to seat further into the cavity or to reach a less stressed position for example.

Prostheses such as femoral implants are durable, but can fail, and the lifetime of the recipient is nowadays very often longer than that of the implant. The technique of revision arthoplasty is hence used to revise the implant—i.e. to remove the failed implant and to replace it with a new one.

At this point, removal of an implant secured by ingrowing bone can be difficult, and it is necessary to chisel or cut down through this bone, around the implant shaft (or a stub left by a fractured implant shaft). This is a lengthy and tiring process for both patient and surgeon, and can result in significant accidental damage to adjacent bone of the walls of the femur.

A range of tools have been proposed to ease this process, including tools activatable with longitudinal-mode ultrasonic vibrations, many devised by the present inventor. However, such tools are still far from perfect, and surgeons would always benefit from using tools that operate more rapidly, more accurately, more controllably and/or with less effort.

Removal of an implant implanted with bone cement is initially easier. Once the head of the femur is opened, for example, the implant is straightforward to draw out, in most cases, since there is little or no adhesion between the metal implant and the bone cement coating the walls of the cavity in the femur. However, it is then necessary to remove all of the existing solid bone cement from the cavity, in order that fresh bone cement paste can be applied, to mould around the new implant as it is inserted.

This is again a tedious process, especially adjacent a distal end of the cavity, where the cement tends to form a solid terminal plug rather than a thin layer around the cavity walls. Various tools have been proposed and used, again including a number of tools vibratable with longitudinal-mode ultrasonic vibrations, devised by the present inventor (International Patent Applications Nos. WO93/03676 and WO96/20657 show examples). These tools are useful because heating of PMMA by energy transfer from an ultrasonically-vibrating tool or probe easily raises the polymer above its depolymerisation temperature of around 120° C., causing it to soften to a consistency allowing it to be scooped or scraped out as a flowable paste, rather than having to be chipped or ground out as a solid. Careful acoustic design can also allow differential energisation of the PMMA while avoiding significant heating of bone, for example should there be accidental transitory contact between bone and an activated tip of the tool or head or probe.

However, there are always benefits to the surgeon from improved tools that operate faster, more accurately, more controllably and/or with less effort.

Additionally, longitudinal-mode ultrasonic vibrations, directed along a probe or tool shaft, can lead to problems, as they characteristically have a distal extensional drilling effect, whether required or not, and they project ultrasound energy a considerable distance longitudinally from a distal tip of the tool/probe. This can lead to tissue damage away from the implant site, and can result in physical bone penetration by said distal tip, even with feedback monitoring to halt such effects by spotting the resonance frequency changes that would occur.

Also, PMMA bone cements and other polymers are nowadays used in other fixation techniques, for example fracture fixation of non-load bearing bones using polymers cured using ultraviolet radiation. This produces a rigid "sausage" of cured polymer extending through a lumen of the fixated bone, across the fracture site. However, once the fracture has healed, removal of the polymer implant is usually indicated, which involves removal of a solid length of polymer. There is hence nowadays a need for equipment that can cope with monolithic bodies of bone cement and other polymers, as well as with thinner layers during metal implant revisions.

Most orthopaedic surgery takes place in relatively cramped geometries. Ideally, even if not "keyhole" surgery, orthopaedic surgery should harm surrounding tissues as little as possible, thus requiring access through as narrow an incision as possible. The geometry of the skeleton and surrounding body tissues may in any case make access to a bone cavity difficult, especially if one is trying to operate along the cavity.

There is hence a need for compact tools that are easily manipulable and can be used in tight spaces. Ultrasonically vibratable tools have a proximal handpiece containing the source of vibrations, generally a stack of piezo-electric ceramic plates mounted to a "horn", which is a sizeable titanium block with a tapering portion, to which a elongate waveguide is fitted, which transmits the ultrasonic vibrations to an operating head, for example. The dimensions and configuration of the stack and horn significantly affect the resonant frequencies and vibrational amplitudes that can be created in a tool, but unfortunately, many current systems thus inevitably have heavy and bulky stack/horn units which the surgeon must hold and manipulate until the tool can be aligned to act on the desired tissues (or bone or cement, as appropriate). It would hence be desirable to provide more compact and lightweight stack/horn arrangements, or alternatives to such arrangements, to ease their use.

Lastly, the precision required of a surgeon can become unreasonable. For example, when working longitudinally down a cavity, through bone holding an implant to an interior of a femur, a very slight inaccuracy could lead to the tip of the tool veering outwardly and damaging the bone of the femoral wall, or alternatively slanting inwardly and contacting the implant, potentially damaging the tool. It would therefore be beneficial if guidance could be provided for the operation of such elongate tools.

It is hence an object of the present invention to provide ultrasonically-vibratable tools, operative heads/probes/outputs for such tools, ultrasound generators for such tools and/or guidance equipment for such tools that obviate some or all of the drawbacks of known systems, as described above.

BRIEF SUMMARY OF THE INVENTION

According to a first aspect of the present invention, there is provided apparatus to generate torsional-mode ultrasonic vibrations, adapted for use with ultrasonically-vibratable surgical tools, comprising conversion horn means having a frustoconical horn portion extending away therefrom and defining a longitudinal axis of the apparatus, and two axial mode ultrasonic transducer stacks, each comprising a plurality of piezo-electric ceramic elements disposed on a common axis, wherein said transducer stacks are mounted to the conversion horn means at respective points on the opposite sides of the longitudinal axis and spaced equally therefrom, with the common axes of the transducer stacks each extending substantially perpendicularly to the longitudinal axis but offset therefrom and each extending parallelly to the other, whereby motion of the transducer stacks exerts a rotational moment about the longitudinal axis, and wherein one, optionally two elongate straight slot means extend longitudinally along a conical surface of the frustoconical horn portion.

Preferably, said two slot means are located on symmetrically opposite sides of the frustoconical horn portion.

Advantageously, said slot means are substantially identical

The slot means may have a length of at least three times their width, optionally at least four times their width.

The slot means may have a depth around half of its width.

A proximal portion of the conversion horn means, to which the transducer stacks are mounted, may have a generally elliptical profile with a ratio of the major and minor axes of said ellipse being between 1.5 and 2.1.

Preferably, a separation between the respective common axes of the two transducer stacks is less than half the wavelength of ultrasonic vibrations in the conversion horn means.

Advantageously, said transducer stacks are symmetrically mounted to the conversion horn means.

In a preferred embodiment, the means to generate torsional mode ultrasonic vibrations is adapted to operate at a frequency of 30 kHz or greater.

Advantageously, the means to generate torsional mode ultrasonic vibrations is adapted to operate at a frequency of 50 kHz or greater.

The means to generate torsional mode ultrasonic vibrations may be adapted to operate at a frequency of up to 80 kHz.

According to a second aspect of the present invention, there is provided a first ultrasonically-activatable tool for removal of polymeric material from a bone cavity, comprising means to generate torsional-mode ultrasonic vibrations, elongate waveguide means extending therefrom for transmission of said ultrasonic vibrations, and operative head means mounted to a distal tip of the waveguide means, wherein the operative head means has a profile that is axisymmetric about a longitudinal axis of the waveguide means, having a concave face aligned distally of the apparatus and a convex face aligned proximally, and the operative head means comprises a plurality of radial slot means, extending through the operative head means between the concave and convex faces thereof and extending radially inwardly from a circumference of the operative head means towards said longitudinal axis of the waveguide means.

In a preferred embodiment, said means to generate torsional-mode ultrasonic vibrations comprises apparatus to generate torsional-mode ultrasonic vibrations as described in the first aspect above.

Preferably, the operative head means has a bell-shaped profile aligned coaxially with the longitudinal axis of the waveguide means.

Alternatively, the operative head means has a bowl or dish-shaped profile, aligned coaxially with the longitudinal axis of the waveguide means.

Advantageously, said concave and convex faces meet at a circumferential rim.

Said circumferential rim may then comprise a distal tip of the apparatus.

Preferably, a thickness of a wall of the operative head means tapers from an axial region to a circumferential rim of the operative head means.

Preferably, each of the convex and concave surfaces of the operative head comprises a portion of a spherical surface.

Advantageously, a radius of curvature of said spherical convex surface is less than a radius of curvature of said spherical concave surface.

Alternatively, each of the convex and concave surfaces of the operative head may comprise a portion of a paraboloidal surface, or a portion of a hyperboloidal surface.

Preferably, the operative head means comprises a distal projection located substantially centrally of the concave face and extending substantially axially.

Said distal projection may engage with a central lumen of a body of polymeric material so as to guide and align the apparatus along said body of polymeric material in use.

Preferably, each said slot means extends radially approximately half way from the circumference of the operative head means towards the axis.

The waveguide means of the apparatus may comprise step means located adjacent its distal end at a nodal plane of the ultrasonic vibrations therein.

Advantageously, the waveguide means reduces distally in diameter across said step means, so as to amplify an intensity of the torsional ultrasonic vibrations in the distal end of the waveguide and the operative head means.

Shroud means may be provided, encasing the waveguide means, to isolate the waveguide means from adjacent body tissues in use.

Said shroud means may be supported by a series of nodal bosses, extending radially from the waveguide means at nodal planes of the ultrasonic vibrations therein.

In an optional embodiment, the waveguide means of the apparatus extends in a curve along at least part of its length.

In such case, the longitudinal axis of the waveguide means should be considered to comprise a local longitudinal axis at any respective point along its length.

According to a third aspect of the present invention, there is provided a second ultrasonically-activatable tool for removal of polymeric material from a bone cavity, comprising means to generate torsional-mode ultrasonic vibrations, elongate waveguide means extending therefrom for transmission of said ultrasonic vibrations, and operative head means mounted to a distal tip of the waveguide means, wherein the operative head means has a generally hemispherical form with a domed distal face, and comprises a plurality of radial slot means, extending through the operative head means between the domed distal face and a proximal face thereof and extending radially inwardly from a circumference of the operative head means.

In a preferred embodiment, said means to generate torsional-mode ultrasonic vibrations comprises apparatus to generate torsional-mode ultrasonic vibrations as described in the first aspect above.

Preferably, said radial slot means comprise a plurality of first slot means and a plurality of second slot means, the first slot means being broader and extending further inwardly than the second slot means.

There may be more second slot means than first slot means.

Advantageously, the first slot means are spaced equally around the circumference of the operative head means.

According to a fourth aspect of the present invention, there is provided a first ultrasonically-activatable tool for cutting bone adjacent a prosthesis held in a bone cavity, comprising means to generate torsional-mode ultrasonic vibrations, elongate waveguide means extending therefrom for transmission of said ultrasonic vibrations, and a cutting element at a distal tip of the waveguide means, wherein said cutting element has a substantially rectangular profile extending along a majority of its length to its distal end.

In a preferred embodiment, said means to generate torsional-mode ultrasonic vibrations comprises apparatus to generate torsional-mode ultrasonic vibrations as described in the first aspect above.

Preferably, the cutting element is provided with flange means extending outwardly from each corner of said substantially rectangular profile.

Said flange means may also extend along a majority of the length of the cutting element.

Advantageously, the narrower sides of the rectangular profile are about half the length of the wider sides of the profile.

The narrower sides of the rectangular profile may be slightly concave.

The wider sides of the rectangular profile may be substantially flat.

A distal face of the cutting element may optionally be concave.

According to a fifth aspect of the present invention, there is provided a second ultrasonically-activatable tool for cutting bone adjacent a prosthesis held in a bone cavity, comprising means to generate torsional-mode ultrasonic vibrations, elongate waveguide means extending therefrom for transmission of said ultrasonic vibrations and a cutting element at the distal end of the waveguide means, said cutting element comprising a plurality of radially upstanding spline means defined between groove means formed into the waveguide means and extending proximally from its distal end.

In a preferred embodiment, said means to generate torsional-mode ultrasonic vibrations comprises apparatus to generate torsional-mode ultrasonic vibrations as described in the first aspect above.

Preferably, the spline means extend helically along the waveguide means.

Advantageously, the spline means extend proximally from the distal end of the waveguide means by less than one eighth of a wavelength of torsional-mode ultrasonic vibrations in the waveguide means.

The groove means may have a depth of between 10% and 20% of a diameter of the waveguide means.

According to a sixth aspect of the present invention, there is provided a third ultrasonically-activatable tool for cutting bone adjacent a prosthesis held in a bone cavity, comprising means to generate torsional-mode ultrasonic vibrations, elongate waveguide means extending therefrom for transmission of said ultrasonic vibrations and a cutting element at a distal tip of the waveguide means, wherein the cutting element is defined between two slightly concave longitudinal faces converging towards the distal tip and two convex longitudinal faces provided with a plurality of radially extending circumferentially-aligned ridges.

In a preferred embodiment, said means to generate torsional-mode ultrasonic vibrations comprises apparatus to generate torsional-mode ultrasonic vibrations as described in the first aspect above.

According to a seventh aspect of the present invention there is provided a guided surgical tool adapted for cutting bone adjacent a prosthesis held in a bone cavity, comprising means to generate torsional-mode ultrasonic vibrations, elongate waveguide means extending therefrom for transmission of said ultrasonic vibrations and cutting head means at a distal tip of the waveguide means, wherein the tool is mounted on an articulated structure and is provided with sensor means to determine a separation between the cutting head means and a prosthesis, and the articulated structure is controlled in response to the sensor means to maintain a desired said separation.

In a preferred embodiment, said means to generate torsional-mode ultrasonic vibrations comprises apparatus to generate torsional-mode ultrasonic vibrations as described in the first aspect above.

BRIEF DESCRIPTION OF THE DRAWING FIGURES

Embodiments of the present invention will now be more particularly described by way of example and with reference to the drawings of the accompanying Figures, in which:

FIG. 1a is a proximal elevation of the transducer unit of the first surgical tool of FIG. 1;

FIG. 1b is a schematic graph showing vibrational amplitudes along the transducer stacks of the transducer unit of FIG. 1a;

FIG. 2 is a scrap perspective view of a distal operative portion of the first surgical tool of FIG. 1, including a distal cutting head thereof;

FIG. 3 is a schematic distal end elevation of the cutting head of the first surgical tool;

FIG. 4 is a perspective view of a wavelength and cutting head of a second surgical tool embodying the present invention;

FIG. 8 is a scrap perspective view of a distal cutting portion of a fourth surgical tool embodying the present invention;

FIG. 9 is a distal end elevation of the cutting portion of the fourth surgical tool;

FIG. 10 is a scrap side elevation of the cutting portion of the fourth surgical tool;

FIG. 14 is a scrap perspective view of a distal cutting portion of a sixth surgical tool embodying the present invention;

FIG. 15 is a distal end elevation of the cutting portion of the sixth surgical tool;

FIG. 16 is a scrap side elevation of the cutting portion of the sixth surgical tool;

DETAILED DESCRIPTION

Figure 1:
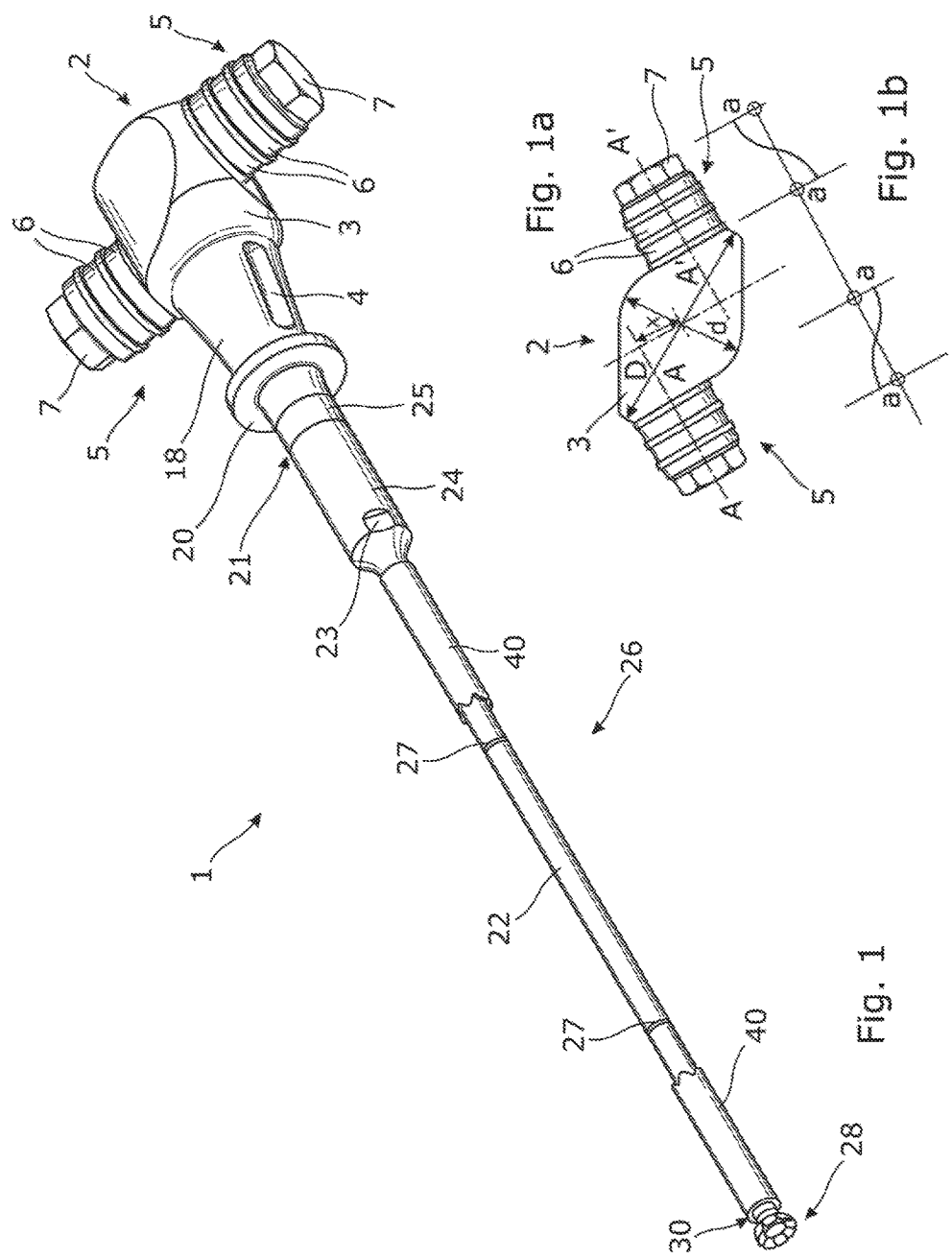
FIG. 1 is a perspective view of a first surgical tool embodying the present invention.

Referring now to the Figures, and to FIG. 1 in particular, a first surgical tool 1 provided with a torsional mode oscillatory system comprises an ultrasonic transducer unit 2, disposed at a proximal end of the tool 1. The transducer unit 2 comprises a torsional converter body 3, to which are mounted a pair of axial-mode ultrasonic transducer stacks 5, each made up of a plurality of axially-polarised piezo-electronic ceramic rings 6, separated by metal electrode rings alternating with the piezo-electric ceramic rings 6 along a central shaft of a threaded bolt 7. The axial-mode ultrasonic transducer stacks 5 are mounted in symmetrical opposition on opposite sides of the torsional converter body 3, at points separated by 180° around its circumference.

As shown, the axial-mode ultrasonic transducer stacks 5 are each mounted to extend outwards, perpendicularly to a longitudinal axis of the transducer unit 2 and a remainder of the tool 1. However, while a longitudinal axis of each stack 5 is aligned at right angles to said longitudinal axis of the transducer 2, the longitudinal axes of each stack 5 are eccentrically spaced from the longitudinal axis of the transducer 2, such that the respective axes do not intersect.

Thus, when the piezo-electric ceramic rings 6 of the transducer stacks 5 are energised with an electrical current having the desired frequency, each transducer stack 5 vibrates axially, but these axial-mode vibrations impinge on the torsional converter body 3 along a line spaced away from its longitudinal axis, almost tangentially. The pair of symmetrically opposed transducer stacks 5, vibrating in phase, thus induce a torsional-mode vibration in the torsional converter body 3 and a remainder of the transducer unit 2.

A major difference between the transducer unit 2 of the present invention and existing ultrasonic transducer units is the presence of a pair of longitudinally-extending slots 4 cut or milled into the converter body 3. As is standard for such transducer units, the torsional converter body 3 comprises a frustoconical horn portion 18, which tapers away from the converter body 3 along the longitudinal axis of the transducer unit 2. Waveguides 22, probes 26 and the like are mountable to a distal end of the horn portion 18 so as to receive ultrasonic vibrations from the transducer unit 1. (See below for details).

In the transducer unit 2 illustrated, a pair of slots 4 extend longitudinally along the frustoconical horn portion 18, spaced 180° apart around its circumference (only one of the pair of slots 4 is thus visible in FIG. 1). Each slot 4 in this exact embodiment is about twice as wide as it is deep. Each slot 4 extends along a majority of the horn portion 18, here extending from adjacent a proximal end of the horn portion 18 to about a slot-width short of mounting flange 20 (see below) which is adjacent the narrower, distal end of the horn portion 18.

These exact proportions may vary with the exact vibrational frequencies to be used. The illustrated apparatus was designed to generate torsional-mode ultrasonic vibrations at a frequency of 65 kHz, the slots 4 each being 15-21 mm long, optimally 18 mm; 2-6 mm wide, optimally 4 mm; 1.25-2.5 mm deep, optimally 1.80 mm constant depth; and terminating 3-5.5 mm from the mounting flange, optimally 4.25 mm. It is believed, however, that the width and depth of the slots 4 should be of the same order of magnitude, and the length of the slots 4 is likely in all cases to be several times greater than their width, possibly three times more.

The presence of the slots 4 allows the transducer unit 2 to be constructed significantly smaller than for existing conventional transducer units capable of generating torsional-mode ultrasonic vibrations of the same frequency and intensity (details below)

FIGS. 1a and 1b show the details of the transducer unit 2 more clearly. The transducer unit 2 comprises the torsional converter body 3, with the two transducer stacks 5 being attached to the converter body 3 adjacent its proximal end. The proximal profile of the converter body 3 is generally elliptical or smoothed lozenge shape, as shown, having a major axis D and a minor axis d. The stacks 5 are fastened to the converter body 3 such that their axes A-A and A'-A' are displaced equal distances x to either side of the common longitudinal axis of the converter body 3 and the horn portion 18.

The elliptical proximal profile of the converter body 3 blends smoothly into the tapering frustoconical horn portion 18 leading to a circular distal output section 25.

The geometrical dimensions of the torsional converter body are critically chosen in relation to the stack 5 size and mass to ensure that the activated converter body 3 and horn portion 18 determine the vibrational mode from the transducer unit 2. An initial drive pulse excites an extensional mode in each axially-polarised piezo-electric ceramic ring 6, which, acting along the offset axes A-A and A'-A' of the two stacks 5 creates a torsionally-directed impulse in the converter body 3.

The dimensions and geometry of the converter body 3 result in a high moment of inertia which is sufficient to generate and sustain a flexural mode of amplitude a in each stack, as shown by FIG. 1b. This mode is sustained by each cycle of the power supply to the rings 6, and so maintains the torsional effect on the converter body 3 and the horn portion 18.

Osecne or two longitudinal slots 4 are machined into the tapering surface of the horn portion 18 of the converter body 3, which remove spurious flexural modes that might be generated in the horn portion 18 and the waveguide 22, ensuring that the output from the distal output section 25 of the converter body 3 is a pure torsional mode.

The ratio of the major axis D to the minor axis d should be between 1.52 and 2.05, ideally 1.7. The ratio of length to diameter for each stack 5 should be between 1.0 and 1.2, ideally 1.1. The axial displacement 2 x between the axes of the stacks 5 (each being x from the longitudinal axis of the converter body 3) should be between 15 and 16 mm, ideally 15.5 mm. The ratio of the diameter of the stack 5 to the minor diameter d of the converter body 3 should be 0.55 to 0.75, ideally 0.65.

Conventional construction based on standard acoustic principles would require that the spacing 2 x between the two stacks 5 should equal half a wavelength of the torsional mode vibrations in the converter body 3. This is much greater than the range for 2 x set out above for the present invention, requiring a much bulkier and heavier converter body 3. Tools using the transducer unit 2 of the present invention are thus much easier to fit into tight spaces and for the surgeon to handle in general, reducing fatigue and improving the quality of the surgical procedures performed.

A mounting flange 20 extends radially outwardly of the horn portion 18 of the torsional converter body 3, adjacent a narrower distal end thereof, and located at a nodal plane of the torsional mode vibrations at a desired, resonant operating frequency. The mounting flange 20 thus allows motional isolation of the ultrasonically-vibratable elements of the tool 1 from contacting mechanical elements (such as an enclosing casing, optionally part of a handpiece to be held by a user) or surrounding biological tissues.

A detachable first probe 26 of the tool 1 is mounted collinearly to a distal output section 25 of the horn portion 18 of the transducer unit 2, by means of a threaded joint, tightened using spanner flats 23. The probe 26 is connected to the distal output section 25 at an antinodal plane 21 of the torsional-mode vibrations at the desired resonant frequency, which represents an output end of the torsional converter body 3.

The detachable probe 26 comprises a proximal generally cylindrical probe input section 24 and an elongate, narrower waveguide 22 extending distally and collinearly therefrom. In the embodiment of FIG. 1, the diameters of the horn distal output section 25 and the proximal probe input section 24 are shown as being equal. However, these may vary in relative diameter, and in some embodiments may be significantly disparate in diameter, according to required input/output characteristics.

The waveguide 22 of the probe 26 is provided with a series of outwardly-extending circumferential bands 27 or bosses, each located at a nodal plane of the torsional-mode ultrasonic vibrations in the waveguide 22 at the desired resonant frequency. A protective sleeve 40 surrounds the waveguide 22 along substantially its entire length, the protective sleeve 40 being isolated from the vibrational waveguide 22 itself by being supported and spaced therefrom by these nodal bands 27 or bosses. The protective sleeve 40 may comprise a durable, heat-resistant plastics material such as poly (ether etherketone) (PEEK) or from stainless steel lined with a heat-resistant, low-friction plastics material.

The probe 26 is provided at a distal end of the waveguide 22 with an operative cutting head feature 28, shown in more detail in FIG. 2. A gain step 30 is provided in this example, adjacent a distal end of the waveguide 22 and adjacent the cutting head feature 28, ideally located at or adjacent a nodal plane of the torsional-mode ultrasonic vibrations at the desired resonant frequency. A nodal gain step 30, reducing the effective diameter of the waveguide 22, yields an increased amplitude (gain) of the torsional-mode ultrasonic vibrations, distal to the nodal gain step 30 and in particular within the cutting head feature 28.

Referring now to FIG. 2, the cutting head feature 28 comprises a generally bell, bowl or dish-shaped body of circular symmetry, aligned coaxially with a longitudinal axis of the waveguide 22. Said body is defined by a convex proximal surface 36 and a concave distal surface 37, the convex proximal surface 36 being more sharply curved than the concave distal surface 37, such that a thickness of the body reduces from a relatively thick axial region to a narrow circumferential rim 38 joining the respective circumferences of the convex 36 and concave 37 surfaces. The circumferential rim 38 of this example extends in a plane perpendicular to the longitudinal axis of the waveguide 22—i.e. it faces wholly distally of the tool 1.

A relatively small axial projection 31 extends from a centre of the concave distal surface 37, substantially collinearly with the waveguide 22. The axial projection 31 is smoothly faired around its periphery into the profile of the concave distal surface 37.

The cutting head feature 28 is segmented by a set of eight (in this embodiment) radially-extending slots 34. Each slot 34 extends completely through the cutting head feature 28 between the convex proximal surface 36 and the concave distal surface 37. Each slot 34 extends radially inwardly from a circumference of the cutting head feature 28, approximately half-way towards the axial projection 31. The slots 34 are spaced equiangularly around the circumference of the cutting head feature 28. These radial slots 34 thus dissect the concave distal surface 37 of the cutting head feature 28 into eight radial facets 35.

This arrangement is more clearly shown in a schematic distal end elevation of the cutting head feature 28, FIG. 3 (note: the circumferential rim 38 is omitted from FIG. 3 for clarity). The cutting head feature 28 thus presents a concave face at a distal end of tool 1 as a whole, with the axial projection 31 at its centre and the slots 34 arranged around its circumference/periphery. Ideally, the circumferential rim 38 is located at an anti-nodal plane of the torsional-mode ultrasonic vibrations.

When the tool 1 is activated, torsional-mode ultrasonic vibrations are generated in the transducer unit 2, and are transmitted along the waveguide 22 to the cutting head feature 28.

For torsional-mode vibrations, the displacement amplitude naturally varies with distance from the axis. There is hence a variation in displacement amplitude both along a longitudinal axis of the tool 1 (due to the nodes and the antinodes of the torsional mode ultrasonic vibrations at the desired resonant frequency) and radially away from said axis, being at a minimum at or adjacent the axis and at a maximum at a periphery/circumference.

The concave distal surface 37 of the cutting head feature 28 is thus brought into contact with plastics material, e.g. within a bone cavity, requiring removal. The torsional displacement amplitude is at a maximum across outer portions of the radial facets 35, The radially-extending edges of the radial facets 35, defining side-walls of the slots 34, will couple particularly well with plastics material entering the slots 34, especially towards the circumference of the cutting head 28. The radial facets 35 and the sidewalls of the slots 34 thus transfer vibrational energy and cause rapid local heating that softens adjacent plastics material. The softened plastics material is then able to flow through the slots 34 to a proximal side of the cutting head feature 28. From here, collected plastics material may be removed from the medullary cavity of the bone by manual manipulation of the tool 1 by the user.

Since the displacement amplitude of the torsional-mode ultrasonic vibrations increases both towards the antinodal plane at the distal tip of the tool 1 and towards a periphery of the cutting head feature 28, the action of the cutting head feature 28 is concentrated in the radial facets 35 and the slots 34, particularly towards the circumferential rim 38. The motional gradient affecting the particulate flow of softened plastics material is also consequently much greater in the cutting head feature 28 of the present invention than in the cutting heads of known tools employing longitudinal-mode/axial-mode vibrations, in which only the variation in displacement amplitude between the nodes and antinodes along the tool would influence particle movement.

The cutting head feature 28 is for the same reasons particularly suitable for removing plastics material arranged in a body around a central channel or lumen (for example, a central lumen of a trauma fixation implant, in which a UV curing probe had been located during implantation, to initiate setting/curing of the plastics material). The axial projection 31 engages with an open end of the channel, acting as a guide for the tool 1, and the cutting head feature 28 is passed longitudinally down the body of plastics material, the radial facets 35 and slots 34 softening and removing the plastics material surrounding the channel.

A body of plastics material in a bone cavity may thus be removed sequentially by passing a series of tools 1 having cutting head features 28 of increasing diameter down an initial channel, widening it with each pass. Eventually, the implant will be sufficiently thinned and weakened that it can be collapsed inwardly into a narrow elongate body and drawn out of the medullary cavity through a correspondingly small cortical fenestration.

Referring now to FIG. 4, a second form of probe 41 is shown, which is mountable to the tool 1 in place of the probe 26 of FIGS. 1 and 2. The second probe 41 is similar, to the first probe 26, having a generally cylindrical proximal probe input section 24 at a proximal end, a cutting head feature 28 at a distal end, and a protective sleeve 40 supported on nodal bands/bosses 27 corresponding to those of the first probe 26. However, the second probe 41 is provided with a narrow, elongate curved waveguide 42, extending from the probe input section 24 to the cutting head feature 28 to transmit torsional-mode ultrasonic vibrations to the cutting head feature 28.

If the curved waveguide 42 is curved in a sufficiently shallow curve of large radius, this interferes very little with the transmission of torsional-mode vibrations. Such a curved waveguide 42 facilitates access for the second probe 41 into a medullary cavity containing plastics material to be removed. Internal fracture/trauma fixation implants of UV-cured plastics material will tend to be harder to access than cement remaining after a metal prosthesis has been removed, and so this feature may be of particular benefit for their revision.

Figure 5:
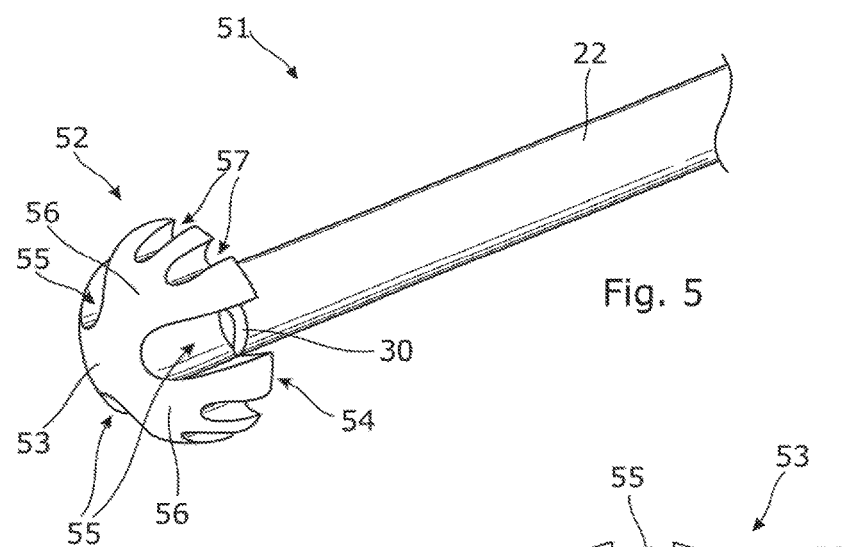
FIG. 5 is a scrap perspective view of a distal operative portion of a third surgical tool embodying the present invention.
Figure 6:
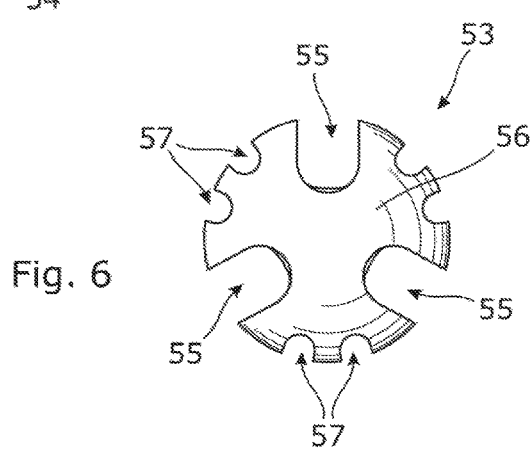
FIG. 6 is a distal end elevation of an operative head of the third surgical tool.
Figure 7:
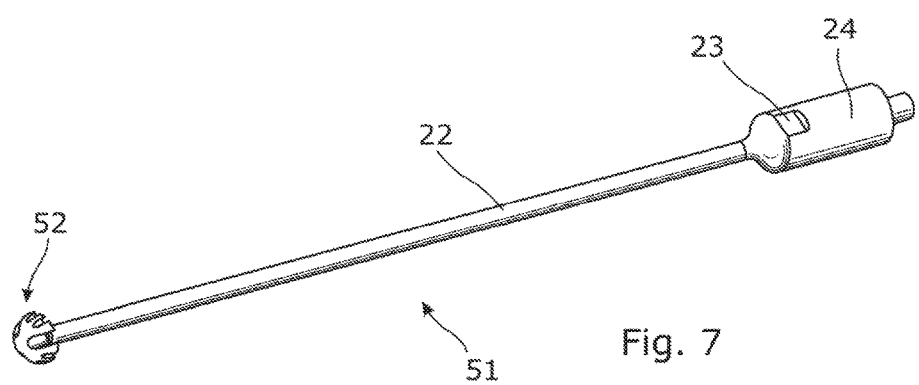
FIG. 7 is a perspective view of a waveguide and operative head of the third surgical tool.

Referring now to FIGS. 5 to 7, the important features of a third surgical tool are illustrated, This third surgical tool ideally comprises a transducer unit 2 identical to that shown in FIG. 1 for the first surgical tool, producing torsional-mode ultrasonic vibrations. FIG. 7 shows a third probe 51 as a whole. The third probe 51 comprises a generally cylindrical proximal probe input section 24 at its proximal end, identical to the probe input section 24 of the first probe 26 and is similarly mountable by a screw-thread mounting to the distal end of the horn portion 18 of the transducer unit 2. The third probe 51 also comprises an elongate, straight waveguide 22, which may be provided with nodally-located radial bosses 27 to support a protective isolating sleeve 40, as for the first probe 26 (omitted from FIG. 7 for clarity). The third probe 51 comprises an operative head 52 at a distal end of the waveguide 22, which is of a different form to the head 28 of the first probe 26, although it is also intended for removal of bone cement from bone cavities. The operative head 52 is shown in more detail in FIGS. 5 and 6.

The operative head 52 has a generally hemispherical form, with a convex, domed distally oriented contact face 53, and a flat or slightly concave proximally-oriented collection face 54 (concealed in these views). The operative head 52 is mounted co-axially by the collection face 54 to a distal end of the waveguide 22, and as in the case of the first probe 26, there is a gain step 30 down to a narrower section of the waveguide 22 adjacent the operative head 52.

The operative head 52 is dissected by three major radial grooves 55 located equiangularly around the head 52 and extending through the head 52 from the domed, distal contact face 53 to the proximal collection face 54. The major radial grooves 55 are sufficiently deep that a base of each major radial groove 55 is generally aligned with an outer diameter of the waveguide 22 (see FIG. 6 in particular). This divides the head 52 into three major lobes 56. Two minor radial grooves 57 are cut into a periphery of each major lobe 56. The relatively shallow minor grooves 57 have a part-circular profile, unlike the much deeper major radial grooves 55 have a more U-shaped profile.

As in the case of the cutting head 28 of the first surgical tool, above, the displacement amplitude across the operative head 52 is greatest adjacent its periphery and least adjacent the longitudinal axis. However the domed, distal contact face 53 is sufficiently broad that when contacted with bone cement or other such plastics material, the transmission of energy is enough to soften the plastics material to the extent that the operative head 52 can be pushed distally further into the plastics material, until its whole contact face 53 is in contact.

The torsional displacement amplitude is greatest in the peripheral portions of the major lobes 56 of the operating head 52, and in radially-extending side-walls of the major and minor radial grooves 55, 57. These hence couple well to the plastics material, transferring vibrational energy and heating and softening the plastics material until it is able to flow through the major radial grooves 55 (and to a lesser extent through the minor radial grooves 57) to the proximal collecting face 54 of the head 52. When the ultrasonic vibrations are halted, this plastics material will solidify and can be removed from the bone cavity by manipulation of the tool by the user.

The third probe 51 may also be used in a retroactive, scraping motion, since a periphery of the proximal collecting face 54 will be at maximum torsional displacement amplitude, and so most effective at softening cement and other plastics materials. The operative head 52 may thus be drawn proximally into contact with plastics material, which will soften, flow and be collectable on the proximal collecting face 54 of the head 52. Preferential use of the major lobes 56 for this purpose will limit the amount of softened material passing through the major radial grooves 55 to the distal face 53 of the head 52.

The torsionally-vibratable tools embodying the present invention avoid the risk of bone penetration that is of concern in known cement removal tools employing longitudinal-mode ultrasonic activation. As mentioned above, longitudinal-mode vibrations direct their energy axially from the distal tip of the tool and have a drilling or chiselling effect on materials contacted by the tip, potentially leading to bone damage of the tool is misdirected or reaches an end of a body of plastics material within a bone cavity. Torsional mode ultrasonic technology avoids this inherent danger by applying a cyclic rotational mode at the cutting face which specifically minimises any such penetrative effect due to contact at the endosteal bone interface.

Referring now to FIGS. 8 to 10, the important features of a fourth surgical tool are illustrated. This fourth surgical tool ideally comprises a transducer unit 2 identical to that shown in FIG. 1 for the first surgical tool, producing torsional-mode ultrasonic vibrations. The fourth surgical tool comprises a fourth probe 71, which comprises a generally cylindrical proximal probe implant portion 24, a coaxially extending narrow, straight waveguide 22 and optionally nodally-located radial bosses 27 supporting an isolating sleeve 40, as for the first and third probes 26, 51.

The fourth probe 71 is intended for cutting bone, to separate an implant from a bone cavity in which it is being held by bone grown between the implant and the cavity walls since implantation. The preferred approach to making these cuts is to insert a cutting tool longitudinally down the cavity, between the implant and the cavity walls, forming a deep, narrow cut. A series of these are made around the circumference of the implant and either joined up or broken with impact tools, thus separating the implant from the bone cavity. Depending on how closely the shaft of the implant approached the walls of the femur, etc, during implantation, the bone to be cut may be cancellous bone or may be tougher cortical bone.

The fourth probe 71 thus has a distal cutting element 72. This has a substantially rectangular cross-section towards its tip, defined by two opposed substantially flat wider lateral faces 74 and two opposed slightly concave narrower lateral faces 75. These lateral faces 74, 75 do not join at the corners of the rectangle that they define; corner flanges 76 project outwardly from each junction of the lateral faces 74, 75, the corner flanges 76 generally following the curvature of the slightly concave narrower lateral faces 75. This provides an overall cross-section akin to a capital I, with the corner flanges 76 as serifs (FIG. 9). The cutting element 72 has this section over most of its length, but there are tapered portions (77, 78 respectively) of the wider lateral faces 74 and the narrower lateral faces 75 at their proximal ends, blending the cross-section of the cutting element 72 into the cylindrical waveguide 22. The distal face 73 of the cutting element is here shown as substantially flat, but a variant has a concave distal face 73 (not shown). This will mean that the distal edge 79 of each narrower lateral face 75 and particularly the associated distal edge of the respective corner flanges 76 will project distally further than a remainder of the distal face 73.

In use, the distal face 73 of the cutting element 72 is presented to an upper surface of the bone connecting the implant and the walls of the bone cavity. Under torsional mode vibration, the displacement amplitude is greater on the narrower lateral faces 75 than on the wider lateral faces 74, as the former are further from the longitudinal axis of the waveguide 22, and this applies to an even greater degree to the corner flanges 76.

The transfer of energy to the contacted bone will hence be greatest along the distal edges 79 of the narrow lateral faces 75 and along the distal edges of the corner flanges 76, even with a flat distal face 73, and if the distal face 73 is concave so that these features contact the bone first, this effect is increased.

The transfer of vibrational energy to bone causes heating, as it does with bone cement, etc, but instead of softening, the pronounced local heating is sufficient to weaken and fragment the bone, locally, faster than the heat could be conducted away through the bone. Manual twisting of the fourth probe 71 about the longitudinal axis thus cuts distally into the bone, allowing the cutting element 72 to be pushed gradually deeper into the bone, generally parallelly to the shaft of the implant, producing the deep, narrow cuts required.

It is also possible to move the cutting element 72 laterally, bringing the corner flanges 76 in particular into contact with bone beside the cut, and so widening the cut.

Such bone cutting probes 71 can be swapped for cement removal probes 26, 41, 51 as required, using the same transducer unit 2. It is only necessary to match the impedance of the probe 71 with that of bone, unlike the probes 26, 41, 51 for which the impedance is optimised for coupling with bone cement, and which only couple weakly to bone to avoid cutting.

Figure 11:
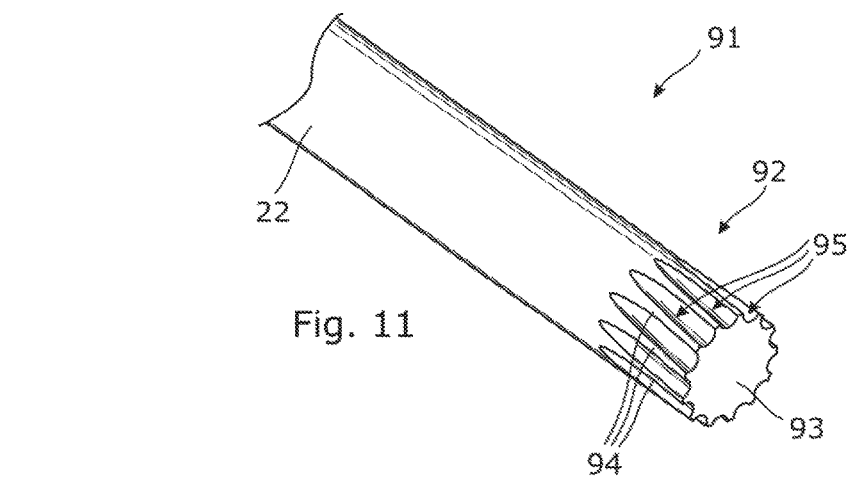
FIG. 11 is a scrap perspective view of a distal cutting portion of a fifth surgical tool embodying the present invention.
Figure 12:
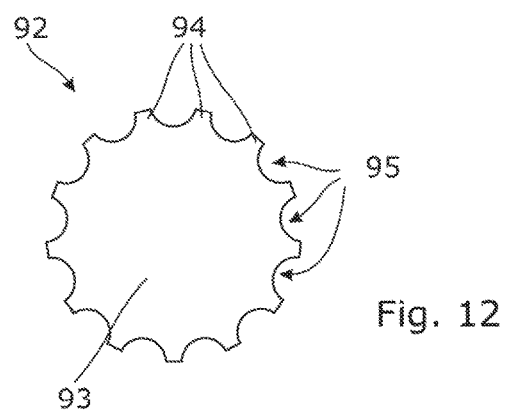
FIG. 12 is a distal end elevation of the cutting portion of the fifth surgical tool.
Figure 13:
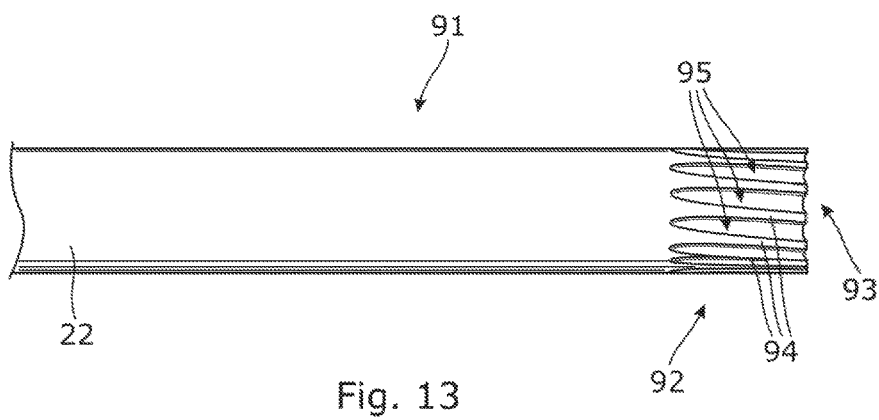
FIG. 13 is a scrap side elevation of the cutting portion of the fifth surgical tool.

FIGS. 11 to 13 show the important features of a fifth surgical tool. This fifth surgical tool ideally comprises a transducer unit 2 identical to that shown in FIG. 1 for the first surgical tool, producing torsional-mode ultrasonic vibrations. FIGS. 11 to 13 show a fifth probe 91, but only its distal cutting element 92. The fifth probe 91 comprises a proximal probe input section 24, an elongate straight waveguide 22 and optionally nodally-located radial bosses 27 to support an isolating sleeve 40, identical to those illustrated for the first probe 26 in FIG. 1.

The fifth probe 91 is intended for cutting bone, to separate an implant from a bone cavity in which it is being held by bone grown between the implant and the cavity walls since implantation. As with the fourth probe 71, it has a distal cutting element 92. This comprises a set of upstanding splines 94, defined by a set of grooves 95 formed in the cylindrical waveguide 22, extending proximally from its distal end 93. The grooves 95 and the splines 94 extend slightly helically, as best seen in FIG. 13. The splines have a height and the grooves 95 have a depth of 10-15% of the overall diameter of the waveguide 22. The grooves 95 become shallower as they extend proximally, the overall length of the splines 94 and grooves 95 from the distal end 93 being less than $\frac{1}{8}\lambda$, where $\lambda$ is the wavelength of torsional-mode ultrasonic vibrations in the waveguide 22. The distal end 93 of the cutting element is slightly concave, such that the tips of the splines 94 project distally (see FIG. 13).

In use, the distal end 93 of the cutting element 92 is presented to an upper surface of the bone connecting the implant and the walls of the bone cavity. Under torsional mode vibration, the displacement amplitude is greater at the circumference of the cutting element 92 at the tips of the splines 94. The radially-extending side walls of the splines 94 also increase the useful area of interaction with the bone and increase the energy transfer from the cutting head 92 to immediately adjacent bone. As in the case of the fourth probe 71, the transfer of vibrational energy to bone causes rapid local heating that weakens and fragments the bone, locally.

The fifth probe 91 thus has an effective distal cutting action into bone. There is only a relatively short cutting element 92, and in any case, this configuration is not optimised for lateral cutting.

FIGS. 14 to 16 illustrate the important features of a sixth surgical tool. This sixth surgical tool ideally comprises a transducer unit 2 identical to that shown in FIG. 1 for the first surgical tool, producing torsional-mode ultrasonic vibrations. Only a distal cutting element 112 of a sixth probe 111 is shown. The sixth probe 111 also comprises a proximal probe input section 24, an elongate straight waveguide 22 and optionally nodally-located radial bosses 27 to support an isolating sleeve 40, identical to those illustrated for the first probe 26 in FIG. 1.

The sixth probe 111 is intended for cutting bone, to separate an implant from a bone cavity in which it is being held by bone grown between the implant and the cavity walls since implantation. As with the fourth probe 71, it has a distal cutting element 112. This has a profile shaped by two opposed concave lateral faces 114, which, as they extend distally towards a distal face 113 of the cutting element 112, broaden, increase in depth and converge towards each other and the axis. The surfaces of the cutting element 112 between the concave lateral faces 114 are convexly curved, corresponding to the circumferential curvature of the waveguide 22. The distal face 113 of the cutting element 112 is distinctly concave, with the result that a distal edge 119 of each convex lateral surface projects distally.

In use, the distal face 113 of the cutting element 112 is presented to an upper surface of the bone connecting the implant and the walls of the bone cavity. Under torsional mode vibration, the displacement amplitude is greater at the circumference of the cutting element 112, i.e. along the distal edges 119. As in the case of the fourth and fifth probes 71, 91 the transfer of vibrational energy to bone causes rapid local heating that weakens and fragments the bone, locally.

The sixth probe 91 thus has an effective distal cutting action into bone. This is enhanced by the presence of multiple circumferentially-extending grooves 115 in the convexly-curved lateral surfaces, defining a series of radially-outstanding ridges 116. The grooves 115 focus vibrational displacement energy into adjacent bone. This sixth probe 111 can have a lateral cutting effect, as well as the distally-oriented effect at the distal face 113.

Figure 17:
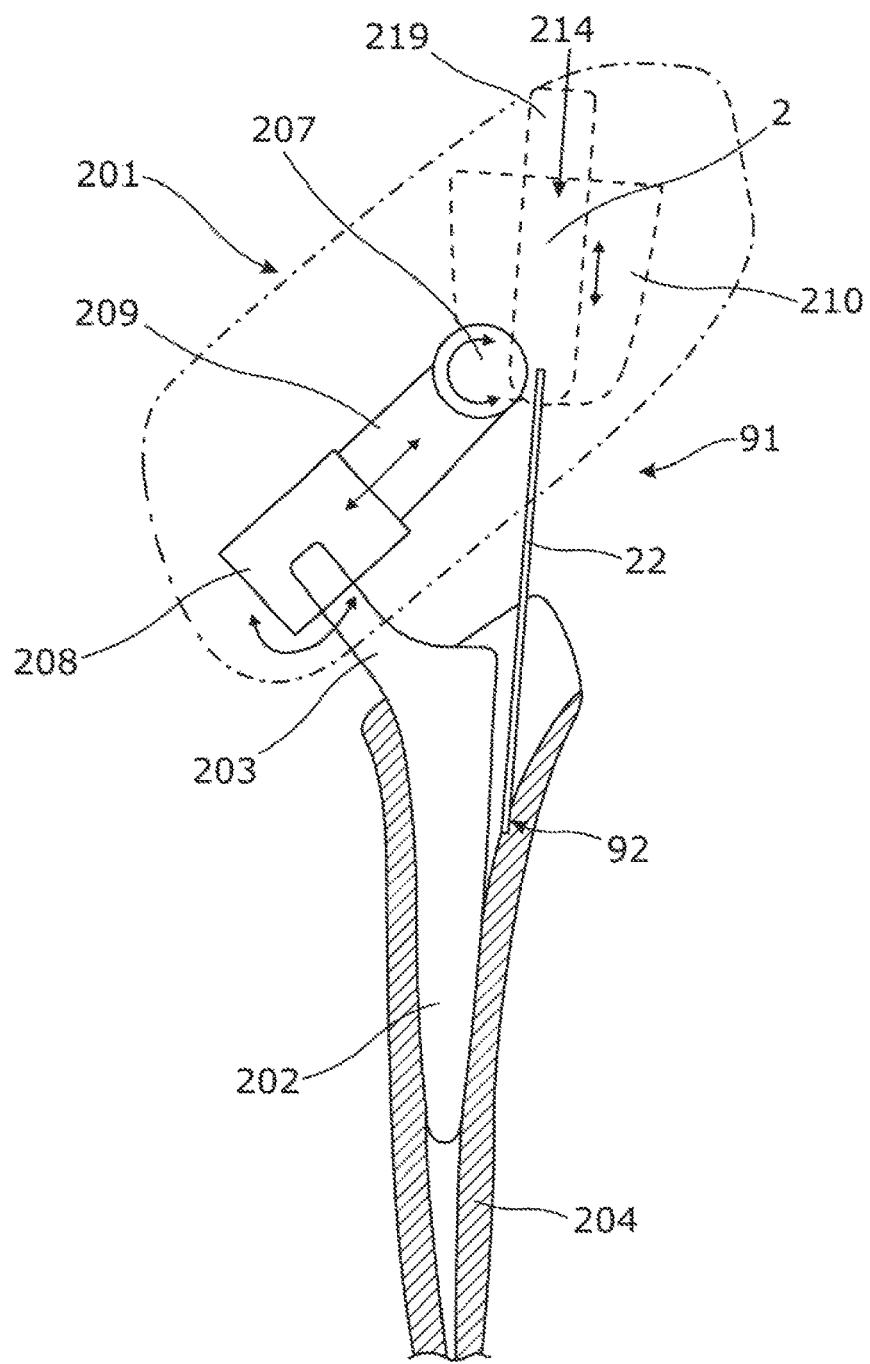
FIG. 17 is a schematic frontal elevation of a seventh, robotically-guided, surgical tool embodying the present invention, mounted to a femoral implant preparatory to freeing the implant from a femur.
Figure 18:
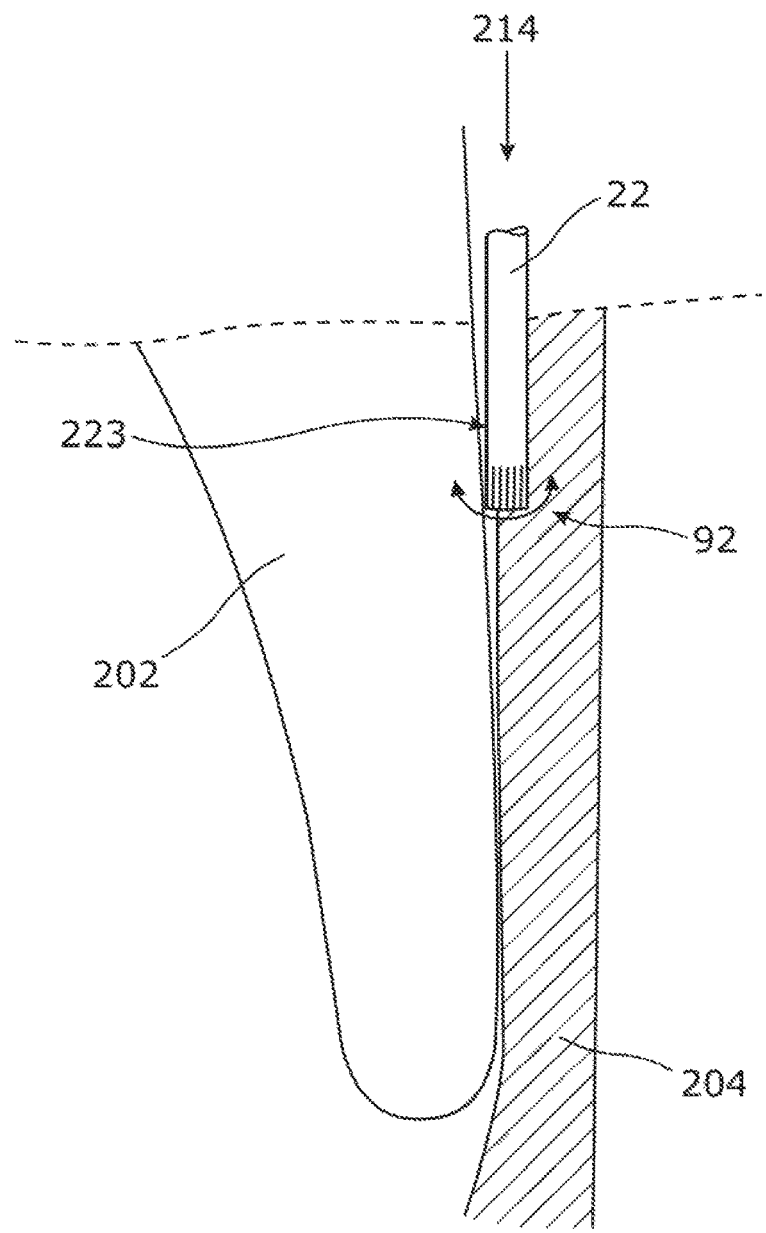
FIG. 18 is a scrap schematic elevation of a distal cutting tip of the seventh surgical tool, in use part-way through a procedure to free the implant.

FIGS. 17 and 18 illustrate a seventh surgical tool 201 of the present invention. This ideally comprises a transducer unit 2 identical to that shown in FIG. 1 of the first surgical tool 1 producing torsional-mode ultrasonic vibrations. It might also be fitted with any of the probes 16, 41, 51, 71, 91, 111 described, although its main use will probably be in bone cutting so the respective bone cutting probes 71, 91, 111 are most likely to be used. The example shown uses the fifth probe 91.

The removal of implants with extensive bony ingrowth over the surface of the prosthesis, particularly its shaft, is known to be much more difficult than for cemented implants, whether the prosthesis is coated with known proprietary coatings to promote this ingrowth, or whether the prosthesis has a specially created porous surface to engage with bone ingrowth. (Both approaches were widely used before it became apparent that revision might become a routine requirement, whether the implant had failed due to component wear, infection, aseptic loosening or other causes). Special bone cutting instruments, including the tools/probes described above, must be used to address the problem of creating separation of the bone/implant interface.

The requirements of such instruments include efficient, safe bone cutting using osteotomes powered by a reliable and compact energy source; means of directing cutting within the narrow interface between the bone and the implant to minimise loss of structural cortical bone in particular; and means of manipulating the instruments to deploy them so as to limit surgeon fatigue and ensure a successful patent outcome.

The fourth to sixth tools described above fulfil many of these requirements, and the torsional mode ultrasound generation arrangements described and suitably compact and effective. Although they are highly effective when manually operated, accurately guiding a long, narrow cut in exactly the desired alignment between bone and implant, multiple times in one procedure, would test the best surgeon. The seventh surgical tool 201 uses feedback-controlled servo-assisted machinery effectively a form of robotics, to improve the accuracy and effectiveness of such tools for revision arthroplasty of "uncemented" orthopaedic implants, especially femoral implants. The seventh surgical tool 201 is generally represented by a dot-dashed outline. A conventional femoral implant 202 is implanted in femur 204, and bone ingrowth is bridging between the wall of the femur 204 and the shaft of the implant 202. Almost all femoral implants have a generally cylindrical neck 203, which when implanted has a ball element of a ball-and-socket joint mounted to its free end, to enable articulation to a socket implanted in the pelvis. In the present invention, the neck 203 of the implant 202 is used as a convenient locating point and datum for the mechanism of the seventh surgical tool 201.

The seventh surgical tool 201 has an articulating mechanism with four degrees of freedom, two rotational and two linear. A first articulation element 208 is located on the neck 203 of the implant 202, and is rotatable within a first plane, as shown by the associated arrow. A second articulation 209 is mounted to the first 208 and can be extended or retracted linearly along a first axis, as shown by the associated arrow. A third articulation element 207 is mounted to the second 209, and is rotatable in a second plane, again as shown by the associated arrow.

Finally, a fourth articulation element 210 is mounted to the third 207, and is moveable reciprocally along a second axis, as shown by the associated arrow. The fourth articulation element 210 has the torsional generator unit 2 attached thereto. Each point of articulation is controllable by conventional servo-motor arrangements.

This allows the waveguide 22 and the cutting element 92 of the fifth probe 91 to be lined up with a desired cutting direction through the bone between the shaft of the implant 202 and femoral wall 204. Manual pressure directed along arrow 214, exerted on a proximal end 219 of the torsional generator unit 2, propels the vibratable cutting element 92 down through the bone.

The cutting element 92 at the tip of the fifth probe 91 is initially easy to position visually adjacent a proximal end of the implant 202, at a bone surface, so that on activation with ultrasonic vibrations it enters the cortical or cancellous bone adjacent the implant 202 shaft/stem.

Sensors (not shown) are provided to monitor a gap 223 (FIG. 18) between the cutting element 92 and the implant 202. These either measure electrical impedance between the implant 202 and the osteotome 92/201 or the capacitive effect of the prosthetic material in close proximity to the osteotome 92/201. The sensors can thus be used to control the servo-motor systems on the articulated elements 207, 208, 209, 210 of the seventh surgical tool 201, so as to adjust the orientation of the cutting element tip 92, and hence the cutting path of the instrument.

In practice, a set distance can be specified for the gap 223, usually between 0.5 mm and 1.5 mm, ideally at 1.0 mm. This keeps the cutting path as close to the implant 202 as is safe, reducing loss of important bone as a result of diverging too far and reducing instrument damage and wear from contacting between the implant 202 and the cutting element 92.

Cutting with a simple manual action, guided by the servo feedback system of the seventh surgical tool 201, is straightforward and less tiring that manipulating corresponding tools. Repetitive cutting by visual alignment with the implant 202 allows a series of narrow substantially parallel bores or channels to be cut through the bone, around as much of the periphery of the implant 202 as desired, followed by joining with lateral cutting and/or breaking the last few joining elements of bone with conventional impact techniques, as desired.

The present invention embodies several features which are essentially absent from alternative systems:
a) Safe torsional operating mode with efficient cement coupling interface; the choice of torsional mode is driven by the need to improve efficiency and at the same time reduce the inherent risk of collateral bone damage;
b) High frequency transducer with balanced twin stack input providing stable resonance in pure torsional mode and additional scope to support large radius curved waveguides;
c) Protective shroud covering majority of waveguide surface and protecting all non-targeted tissue from potential collateral thermal damage;
d) Compactness of the transducer relative to existing transducers of comparable performance, easing manipulation of the tools and reducing user fatigue.

The invention claimed is:

1. Apparatus to generate torsional-mode ultrasonic vibrations, adapted for use with ultrasonically-vibratable surgical tools, comprising conversion horn means having a frustoconical horn portion extending away therefrom and defining a longitudinal axis of the apparatus, and two axial mode ultrasonic transducer stacks, each comprising a plurality of piezo-electric ceramic elements disposed on a common axis, wherein said transducer stacks are mounted to the conversion horn means at respective points on opposite sides of the longitudinal axis and spaced equally therefrom, with the common axes of the transducer stacks each extending substantially perpendicularly to the longitudinal axis but offset therefrom and each extending parallel to the other, whereby motion of the transducer stacks exerts a rotational moment about the longitudinal axis, and wherein at least one elongate slot means extends longitudinally along a conical surface of the frustoconical horn portion.

2. The apparatus to generate torsional-mode ultrasonic vibrations as claimed in claim 1, wherein two said elongate slot means extend longitudinally of the frustoconical horn portion.

3. The apparatus to generate torsional-mode ultrasonic vibrations as claimed in claim 2, wherein said slot means are located symmetrically on opposite sides of the frustoconical horn portion.

4. The apparatus to generate torsional-mode ultrasonic vibrations as claimed in claim 1, wherein a separation between the respective common axes of the two transducer stacks is less than half a wavelength of ultrasonic vibrations in the conversion horn means.

5. The apparatus to generate torsional-mode ultrasonic vibrations as claimed in claim 1 wherein a proximal portion of the conversion horn means, to which the transducer stacks are mounted, has a generally elliptical profile with a ratio of major and minor axes of said generally elliptical profile being between 1.5 and 2.1.

6. An ultrasonically-activatable tool for removal of polymeric material from a bone cavity, comprising the apparatus to generate torsional-mode ultrasonic vibrations as claimed in claim 1, elongate waveguide means extending from the frustoconical horn portion for transmission of said ultrasonic vibrations, and operative head means mounted to a distal tip of the waveguide means, wherein the operative head means has a profile that is axisymmetric about a longitudinal axis of the waveguide means, having a concave face aligned distally of the apparatus and a convex face aligned proximally, and the operative head means comprises a plurality of radial slot means, extending through the operative head means between the concave and convex faces thereof and extending radially inwardly from a circumference of the operative head means towards said longitudinal axis of the waveguide means.

7. The ultrasonically-activatable tool for removal of polymeric material from a bone cavity as claimed in claim 6, wherein the operative head means has a bell-, bowl- or dish-shaped profile aligned coaxially with the longitudinal axis of the waveguide means.

8. The ultrasonically-activatable tool for removal of polymeric material from a bone cavity as claimed in claim 6, wherein said concave and convex faces meet at a circumferential rim comprising a distal tip of the apparatus.

9. The ultrasonically-activatable tool for removal of polymeric material from a bone cavity as claimed in claim 6, wherein the operative head means comprises a distal projection located substantially centrally of the concave face and extending substantially axially.

10. The ultrasonically-activatable tool for removal of polymeric material from a bone cavity as claimed in claim 6, wherein the waveguide means extends in a curve along at least part of its length.

11. An ultrasonically-activatable tool for removal of polymeric material from a bone cavity, comprising the apparatus to generate torsional-mode ultrasonic vibrations as claimed in claim 1, elongate waveguide means extending from frustoconical horn portion for transmission of said ultrasonic vibrations, and operative head means mounted to a distal tip of the waveguide means, wherein the operative head means has a generally hemispherical form with a domed distal face, and comprises a plurality of radial slot means, extending through the operative head means between the domed distal face and a proximal face thereof and extending radially inwardly from a circumference of the operative head means.

12. The ultrasonically-activatable tool for removal of polymeric material from a bone cavity as claimed in claim 11, wherein said radial slot means comprise a plurality of first slot means and a plurality of second slot means, the first slot means being broader and extending further inwardly than the second slot means.

13. The ultrasonically-activatable tool for removal of polymeric material from a bone cavity as claimed in claim 12, wherein there are more second slot means than first slot means.

14. The ultrasonically activatable tool for removal of polymeric material from a bone cavity as claimed in claim

12, wherein the first slot means are spaced equally around the circumference of the operative head means.

15. An ultrasonically-activatable tool for freeing a prosthesis from a bone cavity by cutting through surrounding bone comprising the apparatus to generate torsional-mode ultrasonic vibrations as claimed in claim 1, elongate waveguide means extending from the frustoconical horn portion for transmission of said ultrasonic vibrations, and a cutting element at a distal tip of the waveguide means, wherein said cutting element has a substantially rectangular profile extending along a majority of its length to its distal end.

16. The ultrasonically-activatable tool for freeing a prosthesis from a bone cavity by cutting through surrounding bone in claim 15, wherein the cutting element is provided with flange means extending outwardly from each corner of said substantially rectangular profile.

17. An ultrasonically-activatable tool for freeing a prosthesis from a bone cavity by cutting through surrounding bone, comprising the apparatus to generate torsional-mode ultrasonic vibrations as claimed in claim 1, elongate waveguide means extending from the frustoconical horn portion for transmission of said ultrasonic vibrations, and a cutting element at the distal end of the waveguide means, said cutting element comprising a plurality of radially upstanding spline means defined between groove means formed into the waveguide means, extending proximally from its distal end.

18. The ultrasonically-activatable tool for freeing a prosthesis from a bone cavity by cutting through surrounding bone as claimed in claim 17, wherein the spline means extend helically along the waveguide means.

19. ultrasonically-activatable tool for freeing a prosthesis from a bone cavity by cutting through surrounding bone comprising the apparatus to generate torsional-mode ultrasonic vibrations as claimed in claim 1, elongate waveguide means extending from the frustoconical horn portion for transmission of said ultrasonic vibrations, and a cutting element at a distal tip of the waveguide means, wherein the cutting element is defined between two slightly concave longitudinal faces converging towards the distal tip and two convex longitudinal faces provided with a plurality of radially extending circumferentially-aligned ridges.

20. A guided surgical tool adapted for cutting bone adjacent a prosthesis held in a bone cavity, comprising the apparatus to generate torsional-mode ultrasonic vibrations as claimed in claim 1, elongate waveguide means extending therefrom for transmission of said ultrasonic vibrations and cutting head means at a distal tip of the waveguide means, wherein the tool is mounted on an articulated structure and is provided with sensor means to determine a separation between the cutting head means and a prosthesis, and the articulated structure is controlled in response to the sensor means to maintain a desired said separation.

* * * * *

UNITED STATES PATENT AND TRADEMARK OFFICE
CERTIFICATE OF CORRECTION

| | |
|---|---|
| PATENT NO. | : 10,327,827 B2 |
| APPLICATION NO. | : 15/320604 |
| DATED | : June 25, 2019 |
| INVENTOR(S) | : Young et al. |

Page 1 of 1

It is certified that error appears in the above-identified patent and that said Letters Patent is hereby corrected as shown below:

In the Claims

Column 20, Line 5: Claim 19, Delete "ultrasonically" and insert -- An ultrasonically --

Signed and Sealed this
Twentieth Day of August, 2019

Andrei Iancu
*Director of the United States Patent and Trademark Office*